United States Patent [19]

Faraj

[11] Patent Number: 5,488,176
[45] Date of Patent: Jan. 30, 1996

[54] PREPARATION OF DIALKYL PEROXIDES

[75] Inventor: Mahmoud K. Faraj, Newtown Square, Pa.

[73] Assignee: Arco Chemical Technology, Greenville, Del.

[21] Appl. No.: 373,671

[22] Filed: Jan. 13, 1995

Related U.S. Application Data

[63] Continuation-in-part of Ser. No. 61,408, May 13, 1993, abandoned.

[51] Int. Cl.$^6$ .................................................. C07C 409/16
[52] U.S. Cl. .......................... 568/558.000; 568/559.000
[58] Field of Search ........................................ 568/558, 559

[56] References Cited

U.S. PATENT DOCUMENTS

| | | | |
|---|---|---|---|
| 2,223,807 | 12/1940 | Milas | 368/558 |
| 2,403,758 | 7/1946 | Rust et al. | 568/558 |
| 2,403,771 | 7/1946 | Vaughan et al. | 568/558 |
| 2,630,456 | 3/1953 | Bell et al. | 568/558 |
| 2,862,973 | 12/1958 | Winkler et al. | 568/558 |
| 3,626,014 | 12/1971 | Harvey | 568/558 |
| 3,947,332 | 3/1976 | Vanderpool et al. | 204/86 |
| 4,916,101 | 4/1990 | Lyons et al. | 502/209 |

FOREIGN PATENT DOCUMENTS

| | | |
|---|---|---|
| 839312 | 4/1970 | Canada . |
| 1555308 | 12/1968 | France . |
| 954361 | 4/1964 | United Kingdom . |

OTHER PUBLICATIONS

Milas, et al., J. Am. Chem. Soc., vol. 68, "Studies in Organic Peroxides (VIII)" pp. 250–208 (1946).

Milas, et al., J. Am. Chem. Soc., vol. 68, "Studies in Organic Peroxides (X)", pp. 643–644 (1946).

Davies, et al., J. Chem. Sec., "Organic Peroxides. Part III.", p. 2200 (1954).

*Primary Examiner*—Werren B. Lone
*Attorney, Agent, or Firm*—William C. Long

[57] ABSTRACT

The present invention provides a process for the production of dialkyl peroxides by selective reaction of an alcohol and/or an olefin with a hydrogen peroxide at 70°–110° C. using an inorganic heteropoly and/or isopoly acid catalyst.

7 Claims, No Drawings

PREPARATION OF DIALKYL PEROXIDES

RELATED APPLICATION

This is a continuation-in-part of application Ser. No. 08/061,408 filed May 13, 1993, now abandoned.

BACKGROUND OF THE INVENTION

1. Field of the Invention

The present invention relates to the production of dialkyl peroxides such as ditertiary butyl peroxide by the reaction of an alcohol such as tertiary butyl alcohol and/or an olefin such as isobutylene with hydrogen peroxide in the presence of an inorganic heteropoly and/or isopoly acid catalyst.

2. Description of the Prior Art

The preparation of dialkyl peroxides by the reaction of hydrogen peroxide with tertiary butanol and sulfuric acid is known. See Milas, et al., J. Am. Chem. Soc., Vol. 68, pages 205–208 (1946). Ditertiary amyl peroxide was similarly prepared. See Milas, et al., J. Am. Chem. Soc., Vol. 68, pages 643–644 (1946).

French Patent 1,555,308 shows the production of ditertiary butyl peroxide by the reaction of hydrogen peroxide with isobutylene in the presence of sulfuric acid.

The preparation of dialkyl peroxides by the reaction of an alcohol such as tertiary butyl alcohol (TBA) with an organic hydroperoxide such as tertiary butyl hydroperoxide (TBHP) is known. See, for example, U.S. Pat. Nos. 2,403,771, 2,403,758, 2,862,073, 3,626,014 and the like. The preparation of dialkyl peroxides by the reaction of an olefin such a 2-methylbut-2-ene with an organic hydroperoxide such as TBHP is also known. See Davies, et al., J. Chem. Sec., page 2,200, (1954).

In such prior processes, catalysts such as sulfuric acid, sulfonic acid resins and the like have been employed. The use of such catalysts has a number of disadvantages including the corrosion and safety hazards associated with the use of sulfuric acid, catalyst deactivation and deterioration associated with the use of catalyst resins and the like. Canadian Patent 839,312, for example, shows the production of ditertiary butyl peroxide by the reaction of TBA with TBHP suing a sulfonic acid resin with the requirement that water be azeotropically removed.

The preparation of organic hydroperoxides by reaction of an alcohol such as TBA with hydrogen peroxide using an inorganic heteropoly acid is shown in U.S. Pat. No. 2,630,456.

BRIEF DESCRIPTION OF THE INVENTION

In accordance with the present invention, a process is provided for the selective production of dialkyl peroxides wherein an alcohol and/or an olefin is reacted with hydrogen peroxide in the presence of an inorganic heteropoly or isopoly acid catalyst.

DETAILED DESCRIPTION

The process of the present invention can be represented by the following equations:

$$2 ROH + HOOH \longrightarrow ROOR + 2H_2O \qquad (1)$$

or

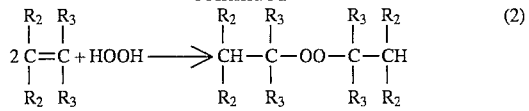

wherein R is an alkyl group having 1 to 10 carbon atoms, $R_2$ and $R_3$ are hydrogen or R. Preferably, R is a tertiary alkyl group having 4 or 5 carbon atoms, i.e. tertiary butyl or tertiary amyl groups, $R_2$ is H and $R_3$ is a methyl or ethyl group.

In especially preferred practice of the invention, ditertiary butyl peroxide is prepared by the reaction of hydrogen peroxide with tertiary butyl alcohol and/or isobutylene, and ditertiary amyl hydroperoxide is prepared by the reaction of hydrogen peroxide with tertiary amyl alcohol and/or tertiary amylene. Dialkyl peroxides where the alkyl groups are different can be prepared for example by reacting mixtures of alcohols and/or mixtures of olefins with hydrogen peroxide.

In carrying out the process of the present invention, for the selective production of dialkyl peroxide it is necessary both that the mol ratio of alcohol and/or olefin to hydrogen peroxide be at least 1 and that elevated temperatures of at least 70° C. be employed. Preferably the mol ratio of alcohol and/or olefin to hydrogen peroxide ranges from 2 to about 5, and the reaction temperature ranges from 70°–110° C. At lower ratios and/or at lower temperatures, high selectivity to dialkyl peroxide is not achieved. In addition, it is essential that the catalyst be employed in amounts sufficient to selectively promote the desired reaction. At least 1 mol of catalyst must be used per 250 mols of alcohol and/or olefin, preferably at least 1 mol of catalyst per 200 mols of alcohol and/or olefin up to about 1 mol of catalyst per 10 mols of alcohol and/or olefin.

In accordance with the invention, the reaction is carried out with selectivity to dialkyl peroxide based on alcohol and/or olefin converted of at least 50%, preferably at least 70% and most preferably at least 80%. In order to achieve the highest selectivities, reaction temperatures of 80°–110° C. are employed with mol ratios of alcohol and/or olefin to hydrogen peroxide of 2–5 and amounts of catalyst of at least 1 mol catalyst per 100 mols alcohol and/or olefin.

The reaction of the invention can be carried out using either alcohol or olefin to react with the hydrogen peroxide. Preferably, however, mixtures of 0.1–10 mols of alcohol per mol of olefin are employed.

The process of the invention is carried out at temperatures sufficiently high to ensure a satisfactory reaction rate and high selectivity but not so high as to cause substantial decomposition of the hydroperoxide. Temperatures ranging from 70° C. to about 110° C. are employed. At lower temperatures substantial amounts of dialkyl peroxide are not formed. The reaction takes place in the liquid phase, and the system pressure is maintained at a level sufficient to ensure the liquid phase reaction. Pressures in the range 0.2– 100 atmospheres gauge are illustrative.

Essential to practice of the invention is the use of the designated amounts of an inorganic heteropoly and/or isopoly acid as catalyst. Such catalysts are water soluble, are highly stable, and are extremely active in promoting the process of the invention. Safety hazards and catalyst deterioration which were encountered in prior art procedures are substantially avoided through the use of these heteropoly or isopoly acid catalysts.

As a class, inorganic heteropoly and isopoly acids, and their preparation are by now quite well known See, for example, "Heteropoly and Isopoly Oxo-metalates", Pope, et al., Springer-Verlag, N.Y., 1983 the contents of which ar incorporated herein by reference. In this regard, reference is also made to U.S. Pat. No. 4,916,101, the disclosure of which is incorporated herein by reference which describes the preparation of heteropoly acid catalysts useful in practice of the present invention. Similarly, U.S. Pat. No. 2,630,456 also describes heteropoly acids useful in catalyzing the reaction of hydrogen peroxide with alcohols to produce hydroperoxides, and the description of heteropoly acids contained therein is also incorporated by reference in the instant case. U.S. Pat. No. 3,947,332 shows preparation of the heteropoly acids also.

Heteropoly acids which are employed in practice of the invention are formed by the condensation of two or more inorganic oxyacids. For example, phosphate and tungstate ions, when reacted in an acidic medium, are condensed to form 12-tungstophosphoric acid, a typical heteropoly acid. In order to function as catalysts in accordance with the invention, the heteropoly anion must be associated with at least one hydrogen cation and preferably all of the cations are hydrogen.

Heteropoly acids of the Keggin structure are most common and are suitable for use in practice of the invention. Acids of the Dawson structure and of other structures can be used.

Illustrative heteropoly acids contain polyatoms selected from molybdenum, tungsten, niobium and vanadium, while the heteroatoms may be phosphorus, boron, germanium, antimony, silicon or the like. Illustrative heteropoly acids include 12-molybdophosphoric acid, 12-tungstophosphoric acid, 12-molybdosilica acid, and 12-tungstosilic acid.

Isopoly acids having vanadate, niobate, molybdate and tungstate anions can be used. Examples are $H_6$ ($H_2$ $W_{12}$ $O_{40}$), $Na_3$ $H_3$ $V_{10}$ $O_{28}$, $Na_4$ $H_5$ $NG_9$ $O_{27}$ and $Na_7$ $H$ $Nb_6$ $O_{19}$. Isopoly acids having mixed isopoly anions can be used.

In practice of the invention sufficient of the heteropoly and/or isopoly acid catalyst is employed to ensure a satisfactory conversion and selectivity. Generally, amounts of catalyst ranging from about 0.1 wt % to about 20 wt%, preferably 0.5 wt% to about 10 wt% based on the weight of the reaction mixture are satisfactorily employed provided the mol ratio criteria above described are met.

In order to more clearly illustrate the invention, the following examples are provided.

EXAMPLE 1

Hydrogen peroxide is reacted with tertiary butyl alcohol in accordance with the invention to form DTBP. About 4.5 grams of 30% aqueous hydrogen peroxide are combined with 0.5 grams of 12-tungstophosphoric acid catalyst ($H_3PW_{12}O_{40}$) and 5.92 grams of tertiary butyl alcohol, and the mixture is heated to 80° C. under a nitrogen blanket. After 4 hours reaction time, 3.50 grams of an organic layer was separated. Analysis of the organic layer showed 20 wt% tertiary butyl alcohol, 34 wt% tertiary butyl hydroperoxide, 35 wt% ditertiary butyl peroxide, 4 wt% acetone and 2.4 wt% methanol.

This example illustrates that even with a 2/1 mol ratio of alcohol to hydrogen peroxide and a reaction temperature of 80° C., at the low catalyst mol ratio used, (1 mol catalyst per 250 mols alcohol) good results are not obtained.

EXAMPLE 2

A series of runs was carried out in order to evaluate the effect of temperature on the reaction of hydrogen peroxide and tertiary butanol to form DTBP. The catalyst employed was 12-tungstophosphoric acid, and the mol ratio of hydrogen peroxide/tertiary butanol/catalyst was 60/60/1. In each case the reaction was carried out under a nitrogen blanket. The following table shows the results which were obtained.

TABLE 1

| Temperature | Conversion % | Selectivity % | | Reaction |
|---|---|---|---|---|
| °C | TBA | TBHP | DTBP | Mixture |
| 50 | 56 | 65 | 22 | 1 phase |
| 70 | 90 | 58 | 37 | 2 phases |
| 85 | 95 | 35 | 60 | 2 phases |

The above results show that higher conversions of tertiary butanol and higher selectivity to ditertiary butyl peroxide are achieved as temperature is increased. Even at a mol ratio of tertiary butanol to hydrogen peroxide of 1, reasonable selectivity to ditertiary butyl peroxide is achieved as reaction temperature is increased.

Comparative Example A

Runs were carried out at 25° C. for the reaction of tertiary butanol with hydrogen peroxide using silica-tungstic acid catalyst, the catalyst to tertiary butanol mol ratio being 1/60. Nitrogen blanket was used. The results are shown in the following Table 2.

TABLE 2

| $TBA/H_2O_2$ Molar Ratio | Time Hours | Con. % TBA | Select. %* TBHP | Wt % DTBP |
|---|---|---|---|---|
| 1 | 5 | 21 | 88 | 3.5 |
| 2 | 5 | 19 | 87 | 2.7 |

*Based on TBA converted.

These data show that at low temperature such as used in Example 1 of U.S. Pat. 2,630,456 only a very low amount of DTBP is produced even with a $TBA/H_2O_2$ molar ratio of 2.

EXAMPLE 3

A series of runs was carried out in order to evaluate the effect of increased amounts of tertiary butanol on the reaction of hydrogen peroxide and tertiary butanol to form DTBP. The catalyst employed was 12-tungstophosphoric acid, and the mol ratio of hydrogen peroxide/catalyst was 60/1. In each case the reaction was carried out at 85° C. under a nitrogen blanket. The following table shows the results which were obtained.

TABLE 3

| $TBA/H_2O_2$ Molar Ratio | Conversion % TBA | Selectivity % | | Reaction |
|---|---|---|---|---|
| | | TBHP | DTBP | Mixture |
| 2 | 76 | 8 | 83 | 2 phases |
| 3 | 63 | 5 | 88.5 | 2 phases |

The above results show that higher selectivity to ditertiary butyl peroxide is achieved as the ratio of tertiary-butanol to hydrogen peroxide is increased where the necessary relatively high reaction temperatures are employed.

We claim:

1. A process for the selective preparation of a dialkyl peroxide which comprises reacting an alcohol and/or olefin with hydrogen peroxide at 70°–120° C. in the presence of an effective amount of an inorganic heteropoly or isopoly acid catalyst, the mol ratio of alcohol and/or olefin to hydrogen peroxide being at least 1, the catalyst being employed in amount of at least 1 mol catalyst per 250 mols of alcohol and/or olefin.

2. A process for the preparation of ditertiary butyl peroxide in at least 50% selectivity based on reacted tertiary butyl alcohol and/or isobutylene which comprises reacting tertiary butyl alcohol and/or isobutylene with hydrogen peroxide at 70°–110° C. in the presence of an effective amount of an inorganic heteropoly and/or isopoly acid catalyst, the mol ratio of tertiary butyl alcohol and/or isobutylene to hydrogen peroxide being at least 1, the catalyst being employed in amount of at least 1 mol catalyst per 250 mols of alcohol and/or olefin.

3. A process for the preparation of ditertiary amyl peroxide in at least 50% selectivity based on reacted tertiary amyl alcohol and/or isoamylene which comprises reacting tertiary amyl alcohol and/or tertiary amylene with hydrogen peroxide at 70°–110° C. in the presence of an effective amount of an inorganic heteropoly and/or isopoly acid catalyst, the mol ratio of tertiary amyl alcohol and/or isoamylene to hydrogen peroxide being at least 1, the catalyst being employed in amount of at least 1 mol catalyst per 250 mols of alcohol and/or olefin.

4. The process of claim 2 wherein the catalyst is an inorganic heteropoly acid catalyst.

5. The process of claim 2 wherein the catalyst is 12-tungstophosphoric acid.

6. The process of claim 2 wherein a mixture of tertiary butyl alcohol and isobutylene containing 0.1–10 mols tertiary butyl alcohol per mol of isobutylene is reacted with hydrogen peroxide.

7. The process of claim 2 wherein the catalyst is employed in amount of at least 1 mol of catalyst per 200 mols of tertiary butyl alcohol and/or isobutylene.

* * * * *

UNITED STATES PATENT AND TRADEMARK OFFICE
CERTIFICATE OF CORRECTION

PATENT NO. : 5,488,176
DATED : January 30, 1996
INVENTOR(S) : Mahmoud K. Faraj

It is certified that error appears in the above-indentified patent and that said Letters Patent is hereby corrected as shown below:

ON THE TITLE PAGE, COLUMN 1:

Under Assignee: Please delete "ARCO Chemical Technology," and insert in its place --ARCO Chemical Technology, L.P.--.

Signed and Sealed this

Seventh Day of May, 1996

Attest:

BRUCE LEHMAN

Attesting Officer

Commissioner of Patents and Trademarks